United States Patent
Lang et al.

(10) Patent No.: US 6,537,328 B1
(45) Date of Patent: *Mar. 25, 2003

(54) KERATINOUS FIBRE OXIDATION DYEING COMPOSITIONS CONTAINING A LACCASE AND DYEING METHOD USING SAME

(75) Inventors: Gérard Lang, Saint Prix (FR); Jean Cotteret, Verneuil sur Seine (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/600,105

(22) PCT Filed: Dec. 21, 1998

(86) PCT No.: PCT/FR98/02807

§ 371 (c)(1),
(2), (4) Date: Sep. 20, 2000

(87) PCT Pub. No.: WO99/36037

PCT Pub. Date: Jul. 22, 1999

(30) Foreign Application Priority Data

Jan. 13, 1998 (FR) .......................... 98 00255

(51) Int. Cl.⁷ .................................. A61K 7/13
(52) U.S. Cl. .................. 8/405; 8/409; 8/412; 8/421; 8/426; 8/594; 8/650; 132/208
(58) Field of Search .................. 8/409, 401, 412, 8/426, 405; 132/208

(56) References Cited

U.S. PATENT DOCUMENTS

| | | | |
|---|---|---|---|
| 3,251,742 A | 5/1966 | Soloway | 167/88 |
| 3,907,799 A | 9/1975 | O'Brien et al. | 260/256 |
| 4,003,699 A | 1/1977 | Rose et al. | 8/10.2 |
| 4,823,985 A | 4/1989 | Grollier et al. | 222/1 |
| 5,061,289 A | 10/1991 | Clausen et al. | 8/405 |
| 5,380,340 A | 1/1995 | Neunhoeffer et al. | 8/409 |
| 5,595,197 A * | 1/1997 | Samain et al. | 132/208 |
| 5,766,576 A | 6/1998 | Löwe et al. | 424/62 |
| 5,769,903 A * | 6/1998 | Audousset et al. | 8/409 |
| 6,004,356 A * | 12/1999 | Audousset et al. | 8/412 |
| 6,010,541 A * | 1/2000 | De la Mettrie et al. | 8/412 |
| 6,045,591 A * | 4/2000 | Deneulenaere et al. | 8/426 |
| 6,090,159 A * | 7/2000 | Maubru et al. | 8/401 |
| 6,090,160 A * | 7/2000 | Junino et al. | 8/409 |
| 6,090,161 A * | 7/2000 | Hoeffkes et al. | 8/409 |
| 6,093,220 A * | 7/2000 | Audousset et al. | 8/412 |
| 6,099,592 A * | 8/2000 | Vidal et al. | 8/409 |
| 6,383,231 B1 * | 5/2002 | Lang et al. | 8/405 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 504 005 | 9/1992 |
| EP | 0 628 559 | 12/1994 |
| FR | 2 112 549 | 6/1972 |
| FR | 2 586 913 | 3/1987 |
| FR | 2 694 018 | 1/1994 |
| FR | 2 733 749 | 11/1996 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/15765 | 5/1996 |
| WO | WO 97/19998 | 6/1997 |
| WO | WO 97/19999 | 6/1997 |

OTHER PUBLICATIONS

English language Derwent Abstract of EP 0 504 005, 9/92.

English language Derwent Abstract of FR 2 112 549, Jun. 16, 1972.

English language Derwent Abstract of FR 2 694 018, Jan. 1994.

English language Derwent Abstract of FR 2 733 749, Nov. 1996.

Vishnu J. Ram et al., "Synthesis of bioisosteric pyrazolo[1,5–a]pyrimidines as leishanicides", Indian Journal of Chemistry, vol. 34B, Jun. 1995, pp. 514–520.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Robert H. Springer et al., "Synthesis and Enzymic Activity of 6–Carbethoxy– and 6–Ethoxy–3,7–disubstituted–pyrazolo[1,5–a]pyrimidines and Related Derivatives as Adenosine Cyclic 3',5'–Phosphate Phosphodiesterase Inhibitors", J. Med. Chem., vol. 25, No. 3, 1982, pp. 235–242.

Thomas Novinson et al., "Synthesis and Antifungal Properties of Certain 7–Alkylaminopyazolo[1,5–a]pyrimidines", J. Med. Chem., vol. 20, No. 2, 1977, pp. 296–299.

(List continued on next page.)

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The invention concerns a ready-to-use oxidation composition for dyeing keratinous fibres, in particular human keratinous fibres such as hair comprising, in a medium suitable for dyeing, at least one oxidation colouring agent, at least an acid direct colouring agent comprising in its structure at least a sulphonic function or at least a carboxylic function, and at least an enzyme such as laccase, as well as the dyeing method using said composition.

44 Claims, No Drawings

OTHER PUBLICATIONS

Alexander McKillop et al., "Reaction of Hydrazine With β–Aminocrotononitrile: Synthesis of 2,–dimethyl–5–Aminopyrazolo[1,5–a]pyrimidine", Heterocycles, vol. 6, Nos. 9, 10, 1977, pp. 1355–1360.

Ermitas Alcalde et al., "Etude de la réaction du β–aminocrotonitrile et du α–formyl phènylacétonitrile avec l'hydrazine: synthèse d'amino–7 pyrazolo[1,5–a]pyrimidines", Journal of Heterocyclic Chemistry, vol. 11, No. 3, Jun. 1974, pp. 423–429.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

English language Derwent Abstract of JP 2–19576, 01/90.

English language Derwent Abstract of JP 5–163124, 6/93.

* cited by examiner

KERATINOUS FIBRE OXIDATION DYEING COMPOSITIONS CONTAINING A LACCASE AND DYEING METHOD USING SAME

The subject of the invention is a composition for the oxidation dyeing of keratinous fibres, and in particular of human keratinous fibres such as hair, comprising, in a medium appropriate for dyeing, at least one oxidation dye, at least one acidic direct dye and at least one enzyme of the laccase type, as well as the dyeing method using this composition.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

It is also known that to further vary the shades obtained and to provide them with shimmer, it is possible to use, in combination with oxidation dye precursors and couplers, direct dyes, that is to say coloured substances which provide a colour in the absence of oxidizing agent.

The vast majority of these direct dyes belong to the family of nitro compounds of the benzene series and have the disadvantage, when they are incorporated into dyeing compositions, of leading to colours with insufficient fastness, in particular towards shampoos.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in U.S. Pat. No. 3,251,742, Patent Applications FR-A-2,112,549, FR-A-2,694,018, EP-A-0, 504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The applicant has now just discovered that it is possible to obtain novel dyes which are capable of giving intense and chromatic colours, without causing significant degradation of the keratinous fibres, which are not very selective and which are quite resistant to various attacks to which the fibres may be subjected, by combining at least one oxidation dye, at least one acidic direct dye comprising in its structure at least one sulphonic function or at least one carboxyl function, and at least one enzyme of the laccase type.

This discovery forms the basis of the present invention.

The first subject of the invention is therefore a ready-to-use composition for the oxidation dyeing of keratinous fibres, and in particular human keratinous fibres such as hair, characterized in that it comprises, in a medium appropriate for dyeing:

at least one oxidation dye, at least one acidic direct dye comprising in its structure at least one sulphonic function or at least one carboxyl function, at least one enzyme of the laccase type.

The ready-to-use dyeing composition in accordance with the invention gives intense and chromatic colours which exhibit low selectivity and excellent properties of resistance both to atmospheric agents such as light and adverse weather conditions and to perspiration and various treatments to which the hair may be subjected (washing, permanent deformation).

The subject of the invention is also a method for the oxidation dyeing of keratinous fibres using this ready-to-use dyeing composition.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense*, in the extracts of Podocarpaceae, *Rosmarinus off., Solanum tuberosum*, Iris sp., Coffea sp., *Daucus carrota, Vinca minor, Persea americana, Catharenthus roseus*, Musa sp., *Malus pumila, Gingko biloba, Monotropa hypopithys* (Indian pipe), Aesculus sp., *Acer pseudoplatanus, Prunus persica, Pistacia palaestina*.

Among the laccases of fungal origin optionally obtained by biotechnology which can be used according to the invention, there may be mentioned the laccase(s) derived from Polyporus versicolor, *Rhizoctonia practicola* and *Rhus vernicifera* as, indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae*, or variants thereof. There may also be mentioned those derived from Tramates versicolor, *Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The lacu unit corresponds to the quantity of enzyme catalysing the conversion of 1 mmol of syringaldazine per minute at pH 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in ulac units.

The quantities of laccase used in the compositions of the invention will vary according to the nature of the laccase chosen. Preferably, they will vary from 0.5 to 2000 ulac, or from 1000 to $4 \times 10^7$ u units, or from 20 to $2 \times 10^6$ ulac units per 100 g of composition.

The nature of the oxidation base(s) and/or of the couplers used in the ready-to-use dyeing composition is not critical.

The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (I) and their addition salts with an acid:

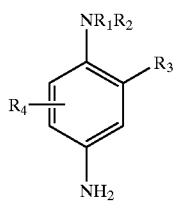

(I)

in which:
$R_1$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_2$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, $R_4$ represents a hydrogen or halogen atom or a $C_1$–$C_4$ alkyl radical.

Among the nitrogen-containing groups of formula (I) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

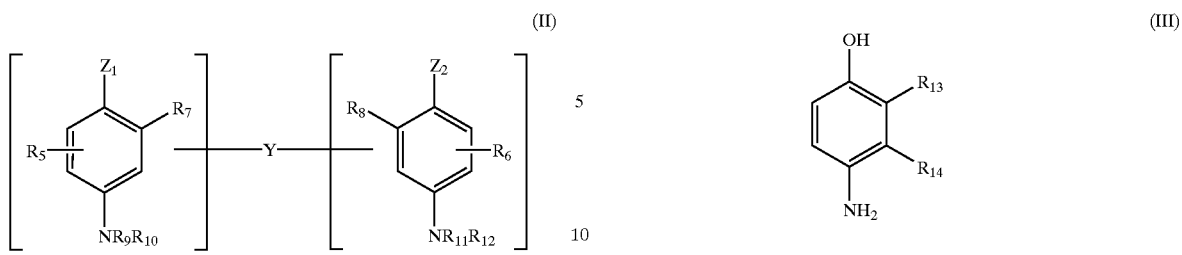

in which:

Z$_1$ and Z$_2$, which are identical or different, represent a hydroxyl or —NH$_2$ radical which may be substituted with a C$_1$–C$_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or C$_1$–C$_6$ alkoxy radicals;

R$_5$ and R$_6$ represent a hydrogen or halogen atom, a C$_1$–C$_4$ alkyl radical, a monohydroxy(C$_1$–C$_4$ alkyl) radical, a polyhydroxy(C$_2$–C$_4$ alkyl) radical, an amino(C$_1$–C$_4$ alkyl) radical or a linking arm Y;

R$_7$, R$_8$, R$_9$, R$_{10}$, R$_{11}$ and R$_{12}$, which are identical or different, represent a hydrogen atom, a linking arm Y or a C$_1$–C$_4$ alkyl radical;

it being understood that the compounds of formula (II) contain only one linking arm Y per molecule.

Among the nitrogen-containing groups of formula (II) above, there may be mentioned in particular the amino, mono(C$_1$–C$_4$)alkylamino, (C$_1$–C$_4$)dialkylamino, (C$_1$–C$_4$) trialkylamino, monohydroxy(C$_1$–C$_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (III), and their addition salts with an acid:

in which:

R$_{13}$ represents a hydrogen or halogen atom, a C$_1$–C$_4$ alkyl, monohydroxy(C$_1$–C$_4$ alkyl), (C$_1$–C$_4$)alkoxy (C$_1$–C$_4$)-alkyl, amino(C$_1$–C$_4$ alkyl) or hydroxy(C$_1$–C$_4$) alkylamino-(C$_1$–C$_4$ alkyl) radical, R$_{14}$ represents a hydrogen or halogen atom, a C$_1$–C$_4$ alkyl, monohydroxy(C$_1$–C$_4$ alkyl), polyhydroxy (C$_2$–C$_4$ alkyl), amino(C$_1$–C$_4$ alkyl), cyano(C$_1$–C$_4$ alkyl) or (C$_1$–C$_4$)alkoxy(C$_1$–C$_4$)alkyl radical, it being understood that at least one of the radicals R$_{13}$ or R$_{14}$ represents a hydrogen atom.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5- hydrazinopyrazole, 1-benzyl-4,5-diamino-3-mephylpyrazole, 4,5-diamino-3-tert-butyl-1-methylplyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylamino-pyrazole, 3,5-diamino-4-(β-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (IV), their addition salts with an acid or with a base and their tautomeric forms, when a tautomeric equilibrium exists:

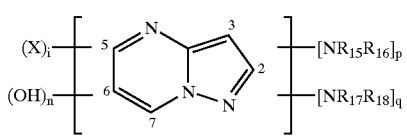

(IV)

in which:

R$_{15}$, R$_{16}$, R$_{17}$ and R$_{18}$, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a (C$_3$–C$_4$)alkoxy(C$_3$–C$_4$ alkyl) radical, a C$_1$–C$_4$ aminoalkyl radical (it being possible for the amine to be protected with an acetyl, ureido or sulphonyl radical), a (C$_3$–C$_4$)alkylamino(C$_1$–C$_4$ alkyl) radical, a di-(C$_1$–C$_4$)alkyl amino(C$_1$–C$_4$ alkyl) radical (it being possible for the dialkyl radicals to form a carbon-containing ring or a 5- or 6-membered heterocycle), a hydroxy(C$_1$–C$_4$)alkyl- or di-[hydroxy (C$_1$–C$_4$)alkyl]-amino(C$_1$–C$_4$ alkyl) radical, the X radicals, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$) alkylamino(C$_1$–C$_4$ alkyl) radical, a di-[(C$_1$–C$_4$)alkyl] amino(C$_1$–C$_4$ alkyl) radical (it being possible for the dialkyls to form a carbon-containing ring or a 5- or 6-membered heterocycle), a hydroxy(C$_1$–C$_4$) alkyl or di-[hydroxy(C$_1$–C$_4$) alkyl]-amino(C$_1$–C$_4$ alkyl) radical, an amino radical, a (C$_1$–C$_4$)alkyl- or di-[(C$_1$–C$_4$)alkyl]-amino radical; a halogen atom, a carboxylic acid group, a sulphonic acid group;

i equals 0, 1, 2 or 3;
p equals 0 or 1;
q equals 0 or 1;
n equals 0 or 1;

With the Proviso That:
the sum p+q is different from 0;
when p+q is equal to 2, then n equals 0 and the groups NR$_{15}$R$_{16}$ and NR$_{17}$R$_{18}$ occupy positions (2,3); (5,6); (6,7); (3,5) or (3,7);
when p+q is equal to 1, then n equals 1 and the group NR$_{15}$R$_{16}$ (or NR$_{17}$R$_{18}$) and the OH group occupy positions (2,3); (5,6); (6,7); (3,5) or (3,7).

When the pyrazolo[1,5-a]pyrimidines of formula (IV) above are such that they comprise a hydroxyl group on one of the positions 2, 5 or 7 at the α position with respect to a nitrogen atom, a tautomeric equilibrium exists which is represented for example by the following scheme:

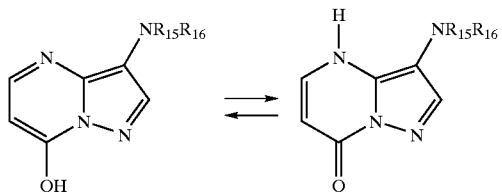

Among the pyrazolo[1,5-a]pyrimidines of formula (IV) above, there may be mentioned in particular:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[.1,5-a]pyrimidine-3,7-diamine;
2,5,N7,N7-tetramethylpyrazolo[1,5-a]pyrimidine-3,7-diamine;

and their addition salts and their tautomeric forms, when a tautomeric equilibrium exists.

The pyrazolo[1,5-a]pyrimidines of formula (IV) above may be prepared by cyclization from an aminopyrazole according to the syntheses described in the following references:

EP 628559 BEIERSDORF-LILLY
R. Vishdu, H. Navedul, Indian J. Chem., 34b(6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN PHARMACEUTICALS The pyrazolo[1,5-a]pyrimidines of formula (IV) above can also be prepared by cyclization from hydrazine according to the syntheses described in the following references:

A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) preferably represent from 0.0005 to 12% by weight approximately of the total weight of the dyeing composition in accordance with the invention, and still more preferably from 0.005 to 6% by weight approximately of this weight.

The coupler(s) which can be used in the ready-to-use dyeing composition in accordance with the invention are those conventionally used in oxidation dyeing compositions, that is to say meta-phenylene-diamines, meta-aminophenols, meta-diphenols, heterocyclic couplers, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

The acidic direct dye(s) which can be used in the ready-to-use dyeing composition in accordance with the invention and comprising at least one sulphonic function can be chosen from the following compounds:

| | |
|---|---|
| (C.I. 10316) | 2,4-dinitro-1-naphthol-7-sulphonic acid, sodium salt |
| (C.I. 10383) | Acid Orange 3 |
| (C.I. 13015) | Acid Yellow 9/Food Yellow 2 |
| (C.I. 14780) | Direct Red 45/Food Red 13 |
| (C.I. 13711) | Acid Black 52 |
| (C.I. 13065) | Acid Yellow 36 |
| (C.I. 14700) | 1-Hydroxy-2-(2',4'-xylyl-5-sulphonatoazo)naphthalene-4-sulphonic acid (sodium salt) (Food Red 1) |
| (C.I. 14720) | Acid Red 14/Food Red 3/Mordant Blue 79 |
| (C.I. 14805) | Acid Brown 4 |
| (C.I. 15510) | Acid Orange 7/Pigment Orange 17/Solvent Orange 49 |
| (C.I. 15985) | Food Yellow 3/Pigment Yellow 104 |
| (C.I. 16185) | Acid Red 27/Food Red 9 |
| (C.I. 16230) | Acid Orange 10/Food Orange 4 |
| (C.I. 16250) | Acid Red 44 |
| (C.I. 17200) | Acid Red 33/Food Red 12 |
| (C.I. 13683) | 1-(3'-Nitro-5'-sulpho-6'-oxophenylazo)-2-oxonaphthalene, Cr. Complex (Acid Red 184) |
| (C.I. 18055) | 1-Hydroxy-2-(4'-acetamidophenylazo)-8-acetamidonaphthalene-3,6-disulphonic acid (sodium salt) (Acid Vioiet 7/Food Red 11) |
| (C.I. 18065) | 1-Hydroxy-2-(2'-methylphenylazo)-8-acetamidonaphthalene-3,6-disulphonic acid (sodium salt) (Acid Red 35) |
| (C.I. 19125) | Acid Violet 3 |
| (C.I. 18130) | Acid Red 135 |
| (C.I. 19130) | Acid Yellow 27 |
| (C.I. 19140) | Acid Yellow 23/Food Yellow 4 |
| (C.I. 20170) | 4'-(sulphonato-2",4"-dimethyl)bis-(2,6-phenylazo)-1,3-dihydroxybenzene (Acid Orange 24) |
| (C.I. 20470) | Acid Black 1 (sodium salt of 1-amino-2-(4'-nitrophenylazo)-7-phenylazo-8-hydroxynaphthalene-3,6-disulphonic acid) |

-continued

| | |
|---|---|
| (C.I. 23266) | (4-((4-Methylphenyl)sulphonyloxy)phenyl-azo)-2,2'-dimethyl-4-((2-hydroxy-5,8-disulphonato)naphthylazo)biphenyl (Acid Red 111) |
| (C.I. 27755) | Food Black 2 |
| (C.I. 25440) | 1-(4'-sulphonatophenylazo)-4-((2"-hydroxy-3"-acetylamino-6", 8"-disulphonato)naphthylazo)-6-sulphonato-naphthalene (tetrasodic salt) (Food Black 1) |
| (C.I. 42080) | 4-β-Hydroxyethylamino-3-nitrobenzene-sulphonic acid |
| (C.I. 42090) | Acid Blue 9 |
| (C.I. 47005) | (5',6' or 7')-Sulphonato-6'-methyl-quinoline-2,2'-Δ-1,3-indanedione (Acid Yellow 3) |
| (C.I. 60730) | Acid Violet 43 |
| (C.I. 61570) | Acid Green 25 |
| (C.I. 62045) | Sodium salt of 1-amino-4-cyclohexane-amino-9,10-anthraquinone 2-sulphonic acid (Acid Blue 62) |
| (C.I. 62105) | Acid Blue 78 |
| — | Acid Blue 156 |
| — | Acid Blue 317 |
| (C.I. 58005) | 1,2-Dihydroxy-3-sulphoanthraquinone (sodium salt) (Mordant Red 3) |
| (C.I. 62055) | 2-Anthracenesulphonic acid, 1-amino-9,10-dihydro 9,10-dioxo-4-(phenylamino) sodium salt |
| (C.I. 14710) | 4-Hydroxy-3-((2-methoxyphenyl)azo)-1-naphthalenesulphonic acid, sodium salt (ACID RED 4) 2-Piperidino 5-nitrobenzenesulphonic acid 2(4'-N,N(2"-hydroxyethyl)amino 2'-nitro)-aniline ethanesulphonic acid |

These dyes are described in particular in the Color Index (published by The Society of Dyers and Colorists, P.O. Box 244, Perkin House, 82 Grattan Road, Bradford, Yorkshire BD1 2JB, ENGLAND).

The sulphonic dyes which are more particularly preferred are the dyes designated in the Color Index under the code C.I. 58005 (monosodium salt of 1,2-dihydroxy-9,10-anthraquinone-3-sulphonic acid), C.I. 60730 (monosodium salt of 2-[(9,10-dihydro 4-hydroxy-9,10-dioxo-1-anthryl) amino]-5-methylbenzene-sulphonic acid), C.I. 15510 (monosodium salt of 4-[(2-hydroxy-1-naphthalenyl)azo] benzenesulphonic acid), C.I. 47005 ([5',6' or 7')sulphonato-6'-methyl-quinoline-2,2'-Δ-1,3-indanedione), C.I. 15985 (disodium salt of 6-hydroxy-5-[(4-sulphophenyl)azo]-2-naphthalenesulphonic acid), C.I. 17200 (disodium salt of 5-amino-4-hydroxy-3-(phenylazo)-2,7-naphthalene-disulphonic acid), C.I. 20470 (disodium salt of 1-amino-2-(41-nitrophenylazo)-7-phenylazo-8-hydroxy-3,6-naphthalenedisulphonic acid), C.I. 42090 (disodium salt of N-ethyl-N-[4-[[4-[ethyl[3-sulphophenyl)methyl]-amino] phenyl](2-sulphophenyl)methylene]-2,5-cyclo-hexadien-1-ylidene]-3-sulphobenzenemethanaminium hydroxide, inner salt), C.I. 61570 (disodium salt of 2,2'-[(9,10-dihydro-9,10-dioxo-1,4-anthracene-diyl)diimino]bis[5-methyl] benzenesulphonic acid.

The acidic direct dye(s) which can be used in the ready-to-use dyeing composition in accordance with the invention and which comprise at least one carboxyl function may be chosen from the following compounds:

4-N-Ethylamino-3-nitrobenzoic acid

2-Piperidino-5-nitrobenzoic acid

4-Amino-2-nitrodiphenylamine-2'-carboxylic acid

4-Amino-4'-dimethylamino-2-nitrodiphenylamine-2'-carboxylic acid

3-Oxo-6-hydroxy-9-carboxyphenylxanthylium acid.

The acidic direct dye(s) which can be used according to the invention preferably represent from 0.001 to 10% by weight approximately of the total weight of the ready-to-use dyeing composition, and more preferably from 0.01 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The medium appropriate for dyeing (or carrier) of the ready-to-use dyeing composition in accordance with the invention generally consists of water or of a mixture of water and of at least one organic solvent in order to solubilize the compounds which might not be sufficiently soluble in water. As organic solvent, there may be mentioned for example $C_1$–$C_4$ alkanols such as ethanol and isopropanol as well as aromatic alcohols such as benzyl alcohol, similar products and mixtures thereof.

The solvents may be present in proportions preferably of between 1 and 40% by weight approximately relative to the total weight of the dyeing composition, and still more preferably between 5 and 30% by weight approximately.

The pH of the ready-to-use composition in accordance with the invention is chosen such that the enzymatic activity of the laccase is sufficient. It is generally between 2 and 11 approximately, and preferably less than 7.

The ready-to-use dyeing composition in accordance with the invention may also contain various adjuvants conventionally used in hair dyeing compositions, such as anionic, cationic, nonionic, amphoteric or zwitterionic surfactants or mixtures thereof, polymers, thickeners, antioxidants, enzymes different from the laccases used in accordance with the invention, such as for example peroxidases or oxidoreductases containing two electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the ready-to-use dyeing composition in accordance with the invention are not, or substantially not, impaired by the addition(s) envisaged.

The ready-to-use dyeing composition in accordance with the invention can be provided in various forms, such as in the form of liquids, creams, gels, optionally pressurized, or in any other,form appropriate for dyeing keratinous fibres, in particular human hair. In this case, the oxidation dye(s) and the laccase(s) are present in the same ready-to-use composition, and consequently the said composition should be free of gaseous oxygen, so as to avoid any premature oxidation of the oxidation dye(s).

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye, at least one acidic direct dye containing a sulphonic or carboxyl function and, on the other hand, a composition (B) containing, in a medium appropriate for dyeing, at least one enzyme of the laccase type, and then in mixing them at the time of use before applying this mixture to the keratinous fibres.

Another subject of the invention is a multi-compartment device or dyeing (kit) or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The following examples are intended to illustrate the invention without limiting the scope as a result.

DYEING EXAMPLE

The following ready-to-use dyeing composition was prepared (contents in grams):

| | |
|---|---|
| para-Phenylenediamine (oxidation base) | 0.283 |
| 5-N-(β-Hydroxyethyl)amino-2-methylphenol (coupler) | 0.283 |
| Sodium salt of 1,2-dihydroxy-9,10-anthraquinone-3-sulphonic acid (C.I. 58005) | 0.300 |
| Laccase derived from Rhus vernicifera laccase containing 180 units/mg sold by the company SIGMA | 1.8 |
| Ethanol | 20 |
| ($C_8$–$C_{10}$)Alkyl polyglucoside in aqueous solution containing 60% of active substance (AS) buffered with ammonium citrate (0.5%), sold under the name ORAMIX CG 110 ® by the company SEPPIC | 4.8 (AS) |
| pH agent qs pH | 6 |
| Demineralized water qs | 100 |

The ready-to-use dyeing composition described above was applied to locks of natural grey hair which is 90% white for 40 minutes and at the temperature of 30° C. The hair was then rinsed, washed with a standard shampoo and then dried.

The hair was dyed in a pink-violet blonde shade.

In the example above, 1.8% of Rhus vernicifera laccase at 180 units/mg can be replaced by 10 1% of Pyricularia Orizae laccase at 100 units/mg sold by the company I.C.N.

What is claimed is:
1. A composition for dyeing keratinous fibers comprising:
   (a) at least one oxidation dye;
   (b) at least one direct dye comprising at least one functional group chosen from sulphonic acid functional groups, carboxylic acid functional groups, and the salts of all said at least one direct dye; and
   (c) at least one enzyme of the laccase type.
2. A composition according to claim 1, wherein said keratinous fibers are human keratinous fibers.
3. A composition according to claim 2, wherein said human keratinous fibers are hair.
4. A composition according to claim 1, wherein said at least one enzyme of the laccase type is chosen from laccases of plant origin, animal origin, fungal origin, bacterial origin and laccases obtained by biotechnology.
5. A composition according to claim 1, wherein said at least one enzyme of the laccase type is chosen from those produced by plants performing chlorophyll synthesis.

6. A composition according to claim 1, wherein said at least one enzyme of the laccase type is chosen from those extracted from plants chosen from Anacardiaceae, Podocarpaceae, *Rosmarinus off., Solanum tuberosum*, Iris sp., Coffea sp., *Daucus Carrota, Vinca minor, Persea americana, Catharenthus roseus*, Musa sp., *Malus pumila, Gingko biloba, Monotropa hypopithys*, Aesculus sp., *Acer pseudoplatanus, Prunus persica* and *Pistacia palaestina*.

7. A composition according to claim 1, wherein said at least one enzyme of the laccase type is chosen from those derived from fungi chosen from *Pyricularia orizae*, Polyporus versicolor, *Rhizoctonia praticola, Rhus vernicifera*, Scytalidium, *Polyporus pinsitus, Myceliophtora thermophila, Rhizoctonia solani, Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all said fungi.

8. A composition according to claim 1, wherein said at least one enzyme of the laccase type is present in a quantity ranging from 0.5 to 2000 ulac units per 100 g of said composition.

9. A composition according to claim 1, wherein said at least one enzyme of the laccase type is present in a quantity ranging from 1000 to $4 \times 10^7$ units per 100 g of said composition.

10. A composition according to claim 1, wherein said at least one enzyme of the laccase type is present in a quantity ranging from 20 to $2 \times 10^6$ ulac units per 100 g of said composition.

11. A composition according to claim 1, wherein said at least one oxidation dye is chosen from oxidation bases, couplers and the acid addition salts of all said at least on oxidation dyes.

12. A composition according to claim 11, wherein said oxidation bases are chosen from para-phenylenediamines, double bases, para-aminophenols, ortho-aminophenols, heterocyclic bases and the acid addition salts of all said oxidation bases.

13. A composition according to claim 12, wherein said para-phenylenediamines are chosen from any of the compounds having the following formula (I) and any of their acid addition salts:

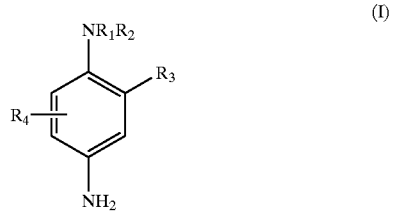

in which:
$R_1$ is chosen from hydrogen atoms, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups, $C_1$–$C_4$ alkyl groups substituted with at least one nitrogen-containing group, phenyl groups and 4'-aminophenyl groups;

$R_2$ is chosen from hydrogen atoms, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups and $C_1$–$C_4$ alkyl groups substituted with at least one nitrogen-containing group;

$R_3$ is chosen from hydrogen atoms, halogen groups, $C_1$–$C_4$ alkyl groups, hydroxy($C_1$–$C_4$ alkyl) groups, hydroxy($C_1$–$C_4$ alkoxy) groups, acetylamino($C_1$–$C_4$ alkoxy) groups, mesylamino($C_1$–$C_4$ alkoxy) groups and carbamoylamino($C_1$–$C_4$ alkoxy) groups; and $R_4$ is chosen from hydrogen atoms, halogen groups and $C_1$–$C_4$ alkyl groups.

14. A composition according to claim 13, wherein said halogen groups are chosen from chlorine, bromine, iodine and fluorine.

15. A composition according to claim 13, wherein said para-phenylenediamines of formula (I) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N, N-diethyl-para-phenylenediamine, N,N-dipropyl-para-phenylenediamine, 4-amino-N,N-diethyl-3-methylaniline, N,N-bis(-hydroxyethyl)-para-phenylenediamine, 4-N,N-bis(-hydroxyethyl)amino-2-methylaniline, 4-N,N-bis(-hydroxyethyl)amino-2-chloroaniline, 2-hydroxyethyl-para-phenylenediamine, 2-fluoro-para-phenylenediamine, 2-isopropyl-para-phenylenediamine, N-(-hydroxypropyl)-para-phenylenediamine, 2-hydroxymethyl-para-phenylenediamine, N,N-dimethyl-3-methyl-para-phenylenediamine, N,N-(ethylhydroxyethyl)-para-phenylenediamine, N-(-dihydroxypropyl)-para-phenylenediamine, N-(4'-aminophenyl)-para-phenylenediamine, N-phenyl-para-phenylenediamine, 2-hydroxyethyloxy-para-phenylenediamine, 2-acetylaminoethyloxy-para-phenylenediamine, N-(-methoxyethyl)-para-phenylenediamine and their acid addition salts.

16. A composition according to claim 12, wherein said double bases are chosen from compounds of the following formula (II) and their acid addition salts:

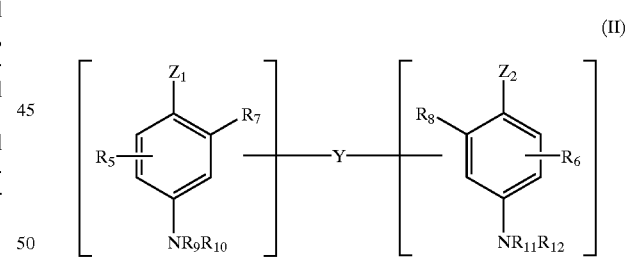

in which:
$Z_1$ and $Z_2$, which may be identical or different, are each chosen from hydroxyl groups and —$NH_2$ groups each of which may optionally be substituted with a group chosen from $C_1$–$C_4$ alkyl groups and linking arms Y;

the linking arm Y is chosen from linear and branched, divalent alkylene groups comprising from 1 to 14 carbon atoms, which optionally may be interrupted by, or which optionally may end with, at least one nitrogen-containing group and/or at least one heteroatom and which optionally may be substituted with at least one group chosen from hydroxyl groups and $C_1$–$C_6$ alkoxy groups;

$R_5$ and $R_6$, which may be identical or different, are each chosen from hydrogen groups, halogen groups, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups and linking arms Y;

$R_7$, $R_8$, $R_9$, $R_{10}$, $R_{11}$ and $R_{12}$, which may be identical or different, are each chosen from hydrogen groups, linking arms Y and $C_1$–$C_4$ alkyl groups;

it being understood that said compounds of formula (II) contain only one linking arm Y per molecule.

17. A composition according to claim 16, wherein said heteroatoms are chosen from oxygen, sulphur and nitrogen atoms.

18. A composition according to claim 16, wherein said double bases of formula (II) are chosen from N,N'-bis(-hydroxyethyl)-N,N'-bis(4'-aminophenyl)-1,3-diaminopropanol, N,N'-bis(-hydroxyethyl)-N,N'-bis(4'-aminophenyl)ethylenediamine, N,N'-bis(4-aminophenyl)tetramethylenediamine, N,N'-bis(-hydroxyethyl)-N,N'-bis(4-aminophenyl)tetramethylenediamine, N,N'-bis(4-methylaminophenyl)tetramethylenediamine, N,N'-bis(ethyl)-N ,N'-bis(4'-amino-3'-methylphenyl)ethylenediamine, 1,8-bis(2,5-diaminophenoxy)-3,5-dioxaoctane, and their acid addition salts.

19. A composition according to claim 12, wherein said para-aminophenols are chosen from compounds corresponding to the formula (III) and their acid addition salts:

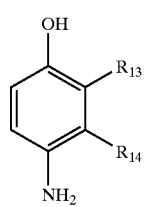

(III)

in which:

$R_{13}$ is chosen from hydrogen atoms, halogen atoms, $C_1$–$C_4$ alkyl groups, hydroxy($C_1$–$C_4$ alkyl) groups, ($C_1$–$C_4$)alkoxy($C_1$–$C_4$)alkyl groups, amino($C_1$–$C_4$) alkylamino($C_1$–$C_4$ alkyl) groups, and hydroxy($C_1$–$C_4$) alkylamino($C_1$–$C_4$ alkyl) groups;

$R_{14}$ is chosen from hydrogen atoms, halogen atoms, $C_1$–$C_4$ alkyl groups, monohydroxy($C_1$–$C_4$ alkyl) groups, polyhydroxy($C_2$–$C_4$ alkyl) groups, amino ($C_1$–$C_4$ alkyl) groups, cyano($C_1$–$C_4$ alkyl)($C_1$–$C_4$)alkyl groups and ($C_1$–$C_4$)alkoxy($C_1$–$C_4$)alkyl groups;

it being understood that at least one of the groups chosen from $R_{13}$ and $R_{14}$ is hydrogen.

20. A composition according to claim 19, wherein said para-aminophenols of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxy-methylphenol, 4-amino-2-aminomethylphenol, 4-amino-2-(hydroxyethyl-aminomethyl)phenol, 4-amino-2-fluoro-phenol and their acid addition salts.

21. A composition according to claim 12, wherein said ortho-aminophenols are chosen from 2-aminophenol, 2-amino-5-methylphenol, 2-amino-6-methylphenol, 5-acetamido-2-aminophenol and their acid addition salts.

22. A composition according to claim 12, wherein said heterocyclic bases are chosen from pyridines, pyrimidines, pyrazoles, pyrazolopyrimidines and their acid addition salts.

23. A composition according to claim 11, wherein said at least one oxidation dye is at least one oxidation base and is present in an amount ranging from approximately 0.0005% to approximately 12.0% by weight relative to the total weight of said composition.

24. A composition according to claim 23, wherein said at least one oxidation dye is at least one oxidation base and is present in an amount ranging from approximately 0.005% to approximately 6.0% by weight relative to the total weight of said composition.

25. A composition according to claim 11, wherein said at least one oxidation dye is at least one coupler chosen from meta-phenylenediamines, meta-aminophenols, meta-diphenols, heterocyclic couplers and the acid addition salts of all said at least one couplers.

26. A composition according to claim 11, wherein said at least one oxidation dye is at least one coupler and is present in an amount ranging from 0.0001% to 10% by weight relative to the total weight of said composition.

27. A composition according to claim 11, wherein said at least one oxidation dye is at least one coupler and is present in a concentration ranging from 0.005% to 5% by weight relative to the total weight of said composition.

28. A composition according to claim 11, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, -naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole, 6-methylpyrazolo[1,5-a]benzimidazole and their acid addition salts.

29. A composition according to claim 1, wherein said at least one direct dye is chosen from compounds designated as C.I. 58005, C.I. 60730, C.I. 15510, C.I. 47005, C. 15985, C.I. 17200, C.I. 20470, C.I. 42090 and C.I. 61570.

30. A composition according to claim 1, wherein said at least one direct dye is chosen from:

4-N-Ethylamino-3-nitrobenzoic acid,

2-Piperidino-5-nitrobenzoic acid,

4-Amino-2-nitrodiphenylamine-2'-carboxylic acid,

4-Amino-4'-dimethylamino-2-nitrodiphenylamine-2'-carboxylic acid, and

3-Oxo-6-hydroxy-9-carboxyphenylxanthylium acid.

31. A composition according to claim 1, wherein said at least one direct dye is present in an amount ranging from 0.001% to 10% by weight relative to the total weight of said composition.

32. A composition according to claim 1, wherein said at least one direct dye is present in an amount ranging from 0.01% to 5% by weight relative to the total weight of said composition.

33. A composition according to claim 1, further comprising at least one carrier appropriate for keratinous fibers.

34. A composition according to claim 33, wherein said at least one carrier is chosen from water and at least one organic solvent.

35. A composition according to claim 34, wherein said at least one organic solvent is present in a concentration ranging from approximately 1% to approximately 40% by weight relative to the total weight of said composition.

36. A composition according to claim 33, wherein said at least one organic solvent is present in a concentration ranging from approximately 5% to approximately 30% by weight relative to the total weight of said composition.

37. A composition according to claim 1, wherein the pH varies from approximately 2 to approximately 11.

38. A composition according to claim 1, wherein the pH is less than 7.

39. A composition according to claim 1, further comprising at least one suitable cosmetic adjuvant chosen from surfactants, polymers, thickeners, antioxidants, enzymes different from said at least one enzyme of the laccases type as defined in claim 1, penetrating agents, sequestering agents, perfumes, buffers, dispersing agents, film-forming agents, screening agents, vitamins, preservatives and opacifying agents.

40. A method of dyeing keratinous fibers comprising applying to said keratinous fibers for a sufficient time to develop a desired color at least one composition comprising:
   (a) at least one oxidation dye;
   (b) at least one direct dye comprising at least one functional group chosen from sulphonic acid functional groups, carboxylic acid functional groups, and the salts of all said at least one direct dye; and
   (c) at least one enzyme of the laccase type.

41. A method of dyeing keratinous fibers according to claim 40, wherein said keratinous fibers are human keratinous fibers.

42. A method of dyeing keratinous fibers according to claim 41, wherein said human keratinous fibers are hair.

43. A method for dyeing keratinous fibres comprising the steps of:
   (a) storing a first composition,
   (b) storing a second composition separately from said first composition,
   (c) mixing the first composition with the second composition to form a mixture, and
   (d) applying said mixture to said keratinous fibres for a time sufficient to achieve a desired colouration,
      wherein said first composition comprises at least one oxidation dye and at least one direct dye comprising at least one functional group chosen from sulphonic acid functional groups, carboxylic acid functional groups, and the salts of all said at least one direct dye, in a medium suitable for keratinous fibres, and
      wherein said second composition comprises at least one enzyme of the laccase type in a medium suitable for keratinous fibres.

44. A multicompartment device or a dyeing kit comprising a first compartment containing a composition (A) comprising, in a medium appropriate for dyeing, at least one oxidation dye and at least one direct dye comprising at least one functional group chosen from sulphonic acid functional groups, carboxylic acid functional groups, and the salts of all said at least one direct dye, and a second compartment containing a composition (B) comprising, in a medium appropriate for keratinous fibers, at least one enzyme of the laccase type.

* * * * *

UNITED STATES PATENT AND TRADEMARK OFFICE
CERTIFICATE OF CORRECTION

PATENT NO. : 6,537,328 B1 Page 1 of 1
DATED : March 25, 2003
INVENTOR(S) : Gérard Lang et al.

It is certified that error appears in the above-identified patent and that said Letters Patent is hereby corrected as shown below:

Column 13,
Line 31, "$4\times 10^7$ units" should read -- $4\times 10^7$ u units --.
Line 39, "least on" should read -- least one --.

Column 14,
Line 22, "N, N-diethyl-para-phenylenediamine," should read -- N,N-diethyl-para-phenylenediamine, --.

Column 15,
Line 20, after "(ethyl)-N", delete the space.

Column 16,
Line 38, "C. 15985," should read -- C.I. 15985 --.

Signed and Sealed this

Thirteenth Day of May, 2003

JAMES E. ROGAN
*Director of the United States Patent and Trademark Office*